(12) United States Patent
Regnier et al.

(10) Patent No.: US 11,497,919 B2
(45) Date of Patent: Nov. 15, 2022

(54) COMMUNICATION AMPLIFICATION DEVICE COMPRISING RETENTION ELEMENTS FOR AN IMPLANTABLE CAPSULE

(71) Applicant: SORIN CRM SAS, Clamart (FR)

(72) Inventors: Willy Regnier, Longjumeau (FR); Jean-Francois Debroux, Saint Etienne de Saint Geoirs (FR)

(73) Assignee: Sorin CRM SAS, Clamart (FR)

( * ) Notice: Subject to any disclaimer, the term of this patent is extended or adjusted under 35 U.S.C. 154(b) by 148 days.

(21) Appl. No.: 17/004,972

(22) Filed: Aug. 27, 2020

(65) Prior Publication Data

US 2021/0077817 A1  Mar. 18, 2021

Related U.S. Application Data

(63) Continuation of application No. 16/062,618, filed on Jun. 14, 2018, now abandoned.

(51) Int. Cl.
*A61N 1/372* (2006.01)
*A61N 1/375* (2006.01)
*A61N 1/05* (2006.01)

(52) U.S. Cl.
CPC ......... *A61N 1/37229* (2013.01); *A61N 1/057* (2013.01); *A61N 1/3756* (2013.01); *A61N 1/37205* (2013.01); *A61N 1/37512* (2017.08); *A61N 1/37518* (2017.08)

(58) Field of Classification Search
CPC . A61N 1/05; A61N 1/08; A61N 1/372; A61N 1/37229; A61N 1/37205
See application file for complete search history.

(56) References Cited

U.S. PATENT DOCUMENTS

| | | |
|---|---|---|
| 2002/0042637 A1 | 4/2002 | Stover |
| 2005/0080346 A1 | 4/2005 | Gianchandani et al. |
| 2005/0137468 A1 | 6/2005 | Avron et al. |
| 2006/0241422 A1 | 10/2006 | Muratayev et al. |
| 2007/0229656 A1 | 10/2007 | Khait et al. |
| 2008/0088397 A1 | 4/2008 | Kretschmer |
| 2009/0281380 A1 | 11/2009 | Miller et al. |
| 2009/0292273 A1 | 11/2009 | Racz et al. |
| 2013/0338452 A1 | 12/2013 | Robertson et al. |
| 2015/0066123 A1 | 3/2015 | Faltys et al. |

OTHER PUBLICATIONS

International Search Report and Written Opinion on International Patent Application No. PCT/EP2016/080877 dated Feb. 23, 2017. 12 pages.

*Primary Examiner* — Jon C Morales
(74) *Attorney, Agent, or Firm* — Foley & Lardner LLP

(57) ABSTRACT

This disclosure relates to a communication amplification device for an implantable capsule, in particular for an autonomous cardiac stimulation capsule. The amplification device comprises a first holding element and a second element configured to hold the implantable capsule. The first holding element is configured to receive the distal end of the capsule and the second holding element is configured to receive the proximal end of the capsule. The first holding element comprises a communication amplification antenna configured to couple to a distal electrode of the capsule.

12 Claims, 3 Drawing Sheets

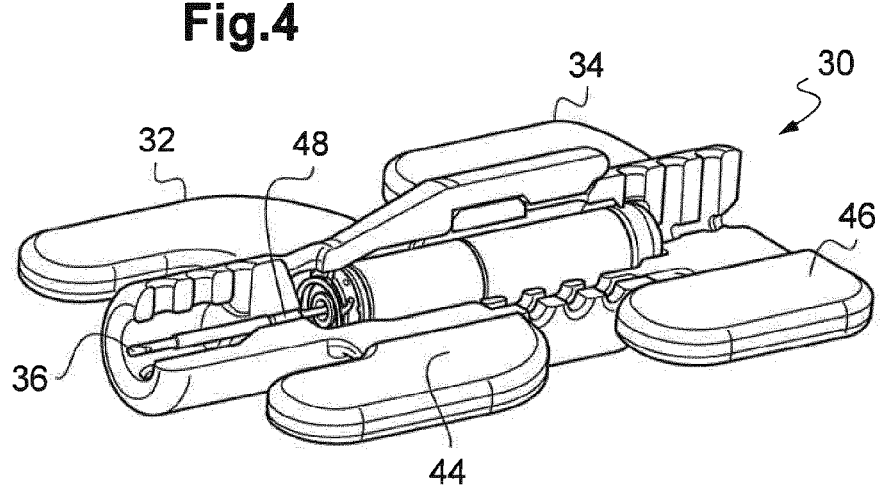
Fig.4
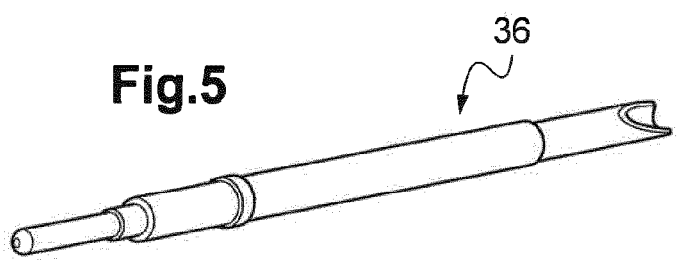
Fig.5
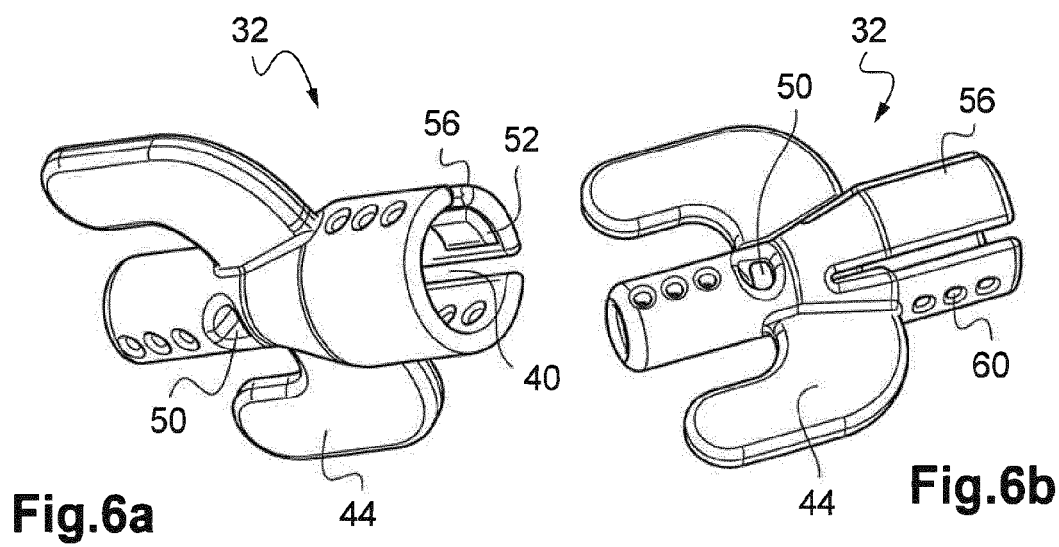
Fig.6a
Fig.6b

COMMUNICATION AMPLIFICATION DEVICE COMPRISING RETENTION ELEMENTS FOR AN IMPLANTABLE CAPSULE

CROSS-REFERENCE TO RELATED PATENT APPLICATIONS

This application is a continuation of U.S. application Ser. No. 16/062,618, filed Jun. 14, 2018, which is a 371 U.S. National Application of International Application No. PCT/EP2016/080877, filed Dec. 14, 2016, which claims the benefit of and priority to French Patent Application No. 1562572, filed Dec. 17, 2015, all of which are incorporated herein by reference in their entireties.

BACKGROUND

The invention relates to "active implantable medical devices" as defined by Council of the European Communities Directive 90/385/EEC of 20 Jun. 1990, and more specifically to pacemaker implants for continuously monitoring heart rate and, if necessary, for delivering electrical pulses to the heart for stimulation, resynchronization, and/or defibrillation, in the event heart arrhythmia is detected by the device.

The invention relates more particularly, but non-limitingly, to such devices that are in the form of a self-contained or "autonomous" capsule designed to be implanted in a cardiac cavity (right or left ventricle or atrium). Such capsules are devoid of any mechanical link or connection to a main device that is either implanted (such as a stimulation or pace-making pulse generator) or not implanted (an external peripheral such as a programmer or monitoring device for remotely monitoring the patient), and, for that reason, they are referred to as "leadless capsules" to distinguish them from sensors that are disposed at the distal end of a conventional lead, through the entire length of which one or more conductors extend that connect the electrode or the sensor metallically to a generator connected to an opposite, proximal end of the lead.

Two categories of autonomous capsules exist. The first category concerns endocardial capsules that are placed in one of the cardiac cavities. The second category concerns epicardial capsules that are fastened to the outer wall of the myocardium, which outer wall is also known as the "epicardium".

Endocardial capsules are of cylindrical shape, e.g. they have a "capsule" shape as shown in FIG. 1, so that they can be inserted longitudinally by an in situ implantation accessory, such as a catheter from the venous or arterial system of the patient.

Fastening means are provided at the end of the capsule for the purpose of anchoring the capsule to the desired stimulation or pace-making site.

An implantable capsule as described in Document US 2008/088397 comprises a body that houses the main component elements of the device (electronic circuits, energy source, stimulation or pace-making electrodes, etc.), and a base secured to the body and rigidly supporting fastening means for fastening to the wall, in particular to the endocardial wall.

Such capsules further comprise a communications device making it possible to communicate with an external device, e.g. a programmer, by radiofrequency or via the human body, in particular by Human Body Communication (HBC) or "intra-body communication", or by any other system, and also to communicate with one or more other implants, for transmitting and receiving information.

As regards implantable autonomous capsules that, for example, use the HBC communication protocol, it is difficult to communicate with such capsules before they are implanted in the patient. For example, one solution consists, during manufacture of an implantable autonomous capsule, in immersing it into a conductive liquid and in also immersing two electrodes into the liquid, which electrodes are connected to an external monitor in order to communicate with the capsule. The liquid is, for example, saline of the 0.9 grams per liter (g/l) sodium chloride (NaCl) type.

However, that solution making it possible to communicate with the implantable autonomous capsule suffers from drawbacks. Firstly, the conductive liquid is not representative of the tissues of the human body. Secondly, communication between the capsule and the external monitor is dependent on the conductivity of the electrodes and of the wires connecting the electrodes to the external monitor.

Such an implantable autonomous device that uses the HBC communication protocol also suffers from the drawback that it is impossible to check whether the system of the capsule is operating properly and to program that capsule once the capsule has been sterilized and placed in a sterile bag.

Checking the system of the capsule is operating properly and programming it can only be achieved by the surgeon, using that immersion method, at the time at which the capsule is being implanted, which gives rise to preoperative risks and additional manipulations of the implantable autonomous capsule that are undesirable when implanting said capsule.

SUMMARY

An object of the present invention is to propose a communication amplification device for an autonomous implantable capsule that makes it possible to avoid having to immerse the implantable capsule in order to communicate with it.

This aspect is particularly critical, insofar as the sterility of the autonomous implantable capsule must be preserved, and it is essential to have good communications between the autonomous implantable capsule and the external device, in order to check the capsule is operating properly and in order to program it.

More specifically, and to this end, the invention provides a communication amplification device for an implantable capsule, in particular for a pacemaker autonomous capsule, the capsule comprising, at its distal end, a distal electrode table to come into contact with the tissue of a wall of an organ of a patient.

In a manner characteristic of the invention, the amplification device comprises a first holding element and a second holding element for holding the implantable capsule, the distal end of the capsule being able to be inserted in the first holding element and the proximal end being able to be inserted in the second holding element, said first holding element comprising a communication amplification antenna, said communication amplification antenna being able to be coupled to the distal electrode of the capsule.

Such a communication amplification device offers the advantage of making it possible to check that the autonomous implantable capsule is operating properly as soon as it has been manufactured. In addition, while it is being prepared for implanting, the implantable capsule may be tested and programmed without being taken out of its sterile packaging.

According to various advantageous subsidiary characteristics:

the communication amplification antenna comprises at least two moving parts that are mounted to move relative to each other, and a spring element enabling the two parts to move relative to each other in order to put the communication amplification antenna in contact with the distal electrode of the capsule;

the communication amplification antenna is formed of a flexible conductive part;

the first holding element comprises a receptacle in which the communication amplification antenna is fastened and which comprises a space enabling the distal electrode of the capsule to be inserted in register with the communication amplification antenna so as to be coupled to said communication amplification antenna;

at its distal end, the capsule comprises an anchor screw comprising turns, and in that the receptacle comprises a shoulder against which the turns of the anchor screw of the capsule come to bear;

the first holding element comprises an opening making it possible to see the coupling implemented between the communication amplification antenna and the distal electrode of the capsule;

the first holding element and the second holding element are table to be assembled together;

the first holding element and/or the second holding element comprise(s) manipulation means;

the first and second holding elements comprise complementary locking means that are suitable for keeping the first holding element and the second holding element locked;

the first holding element and the second holding element comprise manipulation means, the manipulation means of the first and second holding elements being aligned in a horizontal plane when the first and second holding elements are locked together, and the manipulation means of the first and second holding elements form an angle relative to each other when the first and second holding elements are unlocked;

the first and/or the second holding element comprise(s) at least one orifice through the wall of said holding element for the purpose of allowing a fluid to pass into the amplification device; and the second holding element comprises a communication amplification antenna suitable for being put into contact with the proximal electrode of the capsule.

BRIEF DESCRIPTION OF THE DRAWINGS

An embodiment of the present invention is described below with reference to the accompanying drawings, in which like references designate elements that are identical or functionally similar from one figure to another, and in which:

FIG. 4 is cutaway perspective view of a communication amplification device of the invention;

FIG. 5 is a view of a communications antenna designed to be inserted into the amplification device of the invention;

FIGS. 6a and 6b are views of a first holding element in an embodiment of the invention;

DETAILED DESCRIPTION

An embodiment of the invention is described below.

Figure 1:
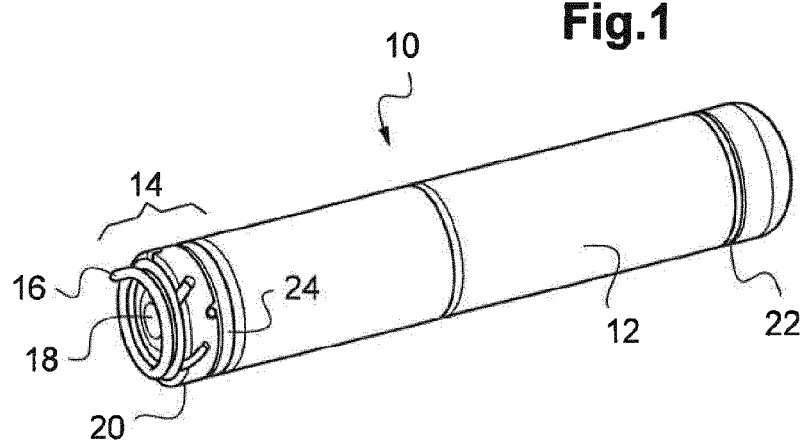
FIG. 1 is an overall perspective view of an implantable capsule.

With reference firstly to FIG. 1, an implantable capsule 10 is shown, which, in this example, is a pacemaker capsule that is an autonomous, i.e. a self-contained, capsule, and which comprises a capsule tubular body 12, and a distal element 14 provided at its distal end with anchor means 16, e.g. of the helical screw type, and with a distal electrode 18.

The anchor means 16 in the form of a screw are formed by a left-handed helically wound wire, and are mounted on an anchor support 20 incorporating arrangements that make the anchoring irreversible. The anchor means 16 are able to come into contact with the tissue of a wall of an organ of the patient.

In a particular embodiment of the autonomous capsule, said capsule comprises an electrical insulation element 24 inserted between the body 12 and the distal element 14 for insulating the distal element from said body.

The body of the capsule 12 houses a set of functional elements of the capsule, in particular an electronics module and a battery, and it also comprises a proximal electrode 22.

Figure 2:
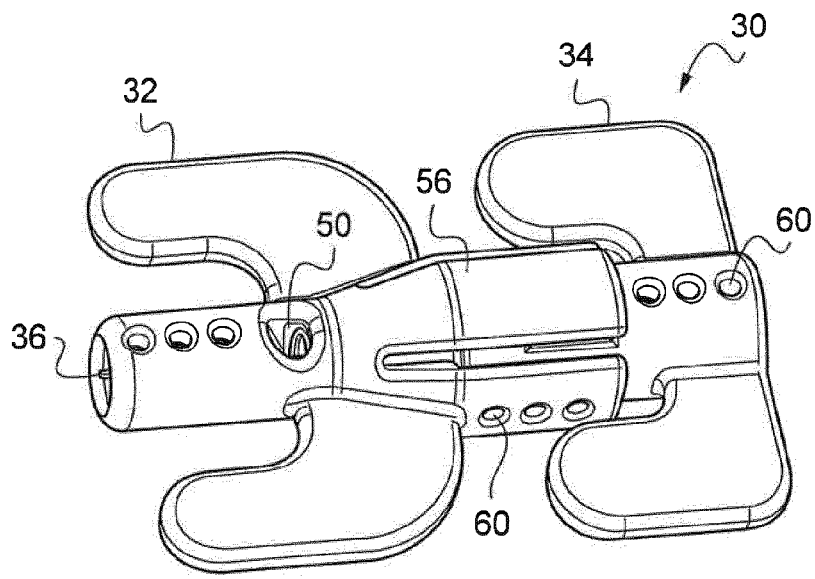
FIG. 2 is an overall perspective view of a communication amplification device of the invention.

FIG. 2 shows a communication amplification device 30 of the invention, in which device an implantable capsule 10, as shown in FIG. 1, is positioned.

The communication amplification device 30 comprises a first holding element 32 and a second holding element 34 for holding the implantable capsule.

The distal end of the capsule 10 is table to be inserted into the first holding element 32, and the proximal end of the capsule is suitable for being inserted into the second holding element 34 of the communication amplification device 30.

Said first holding element 32 comprises a communication amplification antenna 36, which is able to be coupled to the distal electrode 18 of the capsule 10.

Thus, in accordance with the invention, firstly the capsule is held in a communication amplification device and secondly the communication amplification antenna 36 of the device is in contact with the distal electrode 18 of the capsule in order to amplify the signal, in particular the HBC signal, that is delivered by the autonomous capsule.

Thus, it becomes possible to communicate with the capsule from an external device, such as a monitor, before the capsule is implanted, in particular when the assembly formed by the capsule and the amplification device is in its sterile wrapping or packaging. It is thus possible to check that the capsule is operating properly and to program said capsule before performing the operation of implanting the capsule in the patient.

Figure 3:
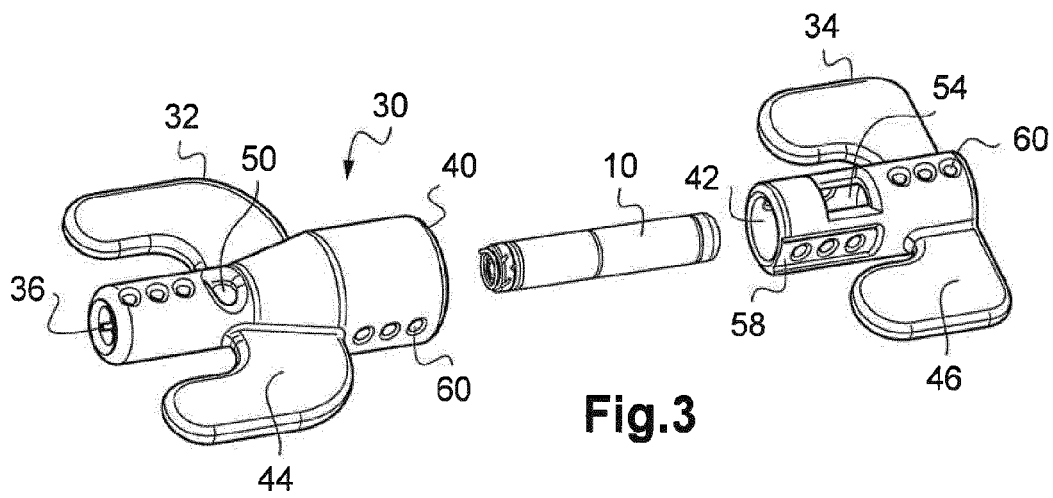
FIG. 3 is a detailed view of the various component elements of a communication amplification device of the invention.

The first holding element 32 and the second holding element 34 of the implantable capsule are, for example, made of plastic. Each of the first and second holding elements 32, 34 has a respective cavity 40, 42 as shown in FIG. 3, dimensioned to fit the outside dimension of the capsule so as to hold the implantable capsule in the amplification device 30.

Such a fit, in particular of the cavity 40 of the first holding element 32 relative to the distal portion of the capsule offers the advantage of maintaining the coupling between the distal electrode 18 of the capsule and the communication amplification antenna 36 of the amplification device.

The communication amplification antenna as coupled in this way to the distal electrode of the capsule increases the length of the conductive part constituted by the distal electrode, and thus makes it possible to increase the radiation of the electric field into its surrounding environment.

In accordance with the invention, the communication amplification device makes it possible to communicate simply and safely with the autonomous capsule when said assembly is placed in its sterile packaging, without having to open the sterile packaging and manipulate the capsule.

As shown in FIG. 2, and in a particular embodiment, the first and second holding elements 32 and 34 are able to be assembled together.

FIG. 3 shows the various elements of the communication amplification device 30, namely the first and second holding element 32, 34, and the capsule 10 coming to be inserted into the holding elements.

The second holding element 34 comprises a cavity 42 of shape complementary to the proximal portion of the capsule.

In the embodiment shown in FIG. 1 and in FIG. 3, the capsule 1 is of cylindrical shape, and the cavity is thus of a cylindrical shape that fits the proximal end of the capsule 10.

In a particular embodiment, in order to facilitate insertion of the proximal portion of the capsule into the second holding element 34, a significant amount of clearance is present between the proximal portion of the capsule and the outline of the cavity 42 in the holding element 34, e.g. about 2 millimeters (mm) of clearance. However, in the low portion of the cavity, the amount of clearance between the proximal portion of the capsule and the low portion of the cavity is smaller so that the proximal portion of the capsule is centered and held. To achieve this, the low portion of the cavity fits relatively snugly over the outside dimension of the proximal portion of the capsule. In an example, the clearance present in the low portion of the cavity lies in the range 0 mm to −0.1 mm.

The first holding element 32 also comprises a cavity of shape complementary to the distal portion of the capsule, in particular of a cylindrical shape that fits the distal end of the capsule 10. In addition, this cavity has a depth such that the capsule is inserted until the distal electrode 18 of the capsule comes to be coupled to the communication amplification antenna 36 positioned in the first holding element 32.

In a particular embodiment, the first holding means comprise a significant amount of clearance between the distal portion of the capsule and the outline of the cavity in the holding element 32, e.g. 2 mm of clearance. However, in the low portion of the cavity, the amount of clearance between the distal portion of the capsule and the low portion of the cavity is smaller so that the distal portion of the capsule is centered. To achieve this, the low portion of the cavity fits relatively snugly over the outside dimension of the distal portion of the capsule. In an example, the clearance present in the low portion of the cavity lies in the range 0 mm to 0.2 mm.

The difference in snugness of fitting described above between the first and the second holding elements and the autonomous capsule enables the surgeon to remove the first holding element from the capsule during implanting, while the capsule remains held by the second holding element, thereby enabling the surgeon to fasten the fitting device to the capsule. This procures easy manipulation for the surgeon.

As shown in FIG. 1 and in FIG. 2, the first and/or second holding means 32, 34 comprise(s) respective manipulation means 44, 46 so that the two holding elements can be taken hold of easily by the surgeon. For example, the manipulation means 44 and 46 may be protuberances positioned on either side of the body of each of the holding elements.

FIGS. 4, 6a, and 6b show an embodiment of the first holding element 32 in detail.

The first holding element 32 comprises a receptacle 48, at the bottom of the cavity 40, in which receptacle the communication amplification antenna 36 is fastened and which receptacle comprises a space enabling the distal electrode 18 of the capsule to be inserted in register with the communication amplification antenna 36 so as to be coupled to said communication amplification antenna 36.

At its distal end, the capsule as shown in particular in FIG. 1 comprises an anchor screw 16 comprising turns.

In an embodiment, in order to facilitate putting the distal electrode 18 into contact with the communication amplification antenna 36, the first holding element 32, in particular the receptacle 48 of said first holding element, comprises a shoulder against which the turns of the anchor screw 16 of the capsule come to bear so as to move the turns of the anchor screw 16 closer together and so as to give improved access to the distal electrode 18.

In particular, the receptacle has a cylindrical shape in which the shoulder is housed. The shoulder makes it possible to define a space, in particular a hollow cylindrical space, into which the distal electrode comes to be inserted. The space created by said shoulder is substantially of the same diameter as the distal electrode.

For example, the distal electrode 18 of the capsule is dome-shaped, or is pointed, or is plane.

The communication amplification antenna 36 inserted into the first holding element 32 comprises an end that is inserted into the space created in the shoulder. The communication amplification antenna 36 is positioned in such a manner as to come into contact with the face of the distal electrode 18 of the capsule when the capsule is centered in the first holding element 32 in an embodiment.

FIG. 5 shows in detail an embodiment of the communication amplification antenna 36.

The communication amplification antenna in the example shown comprises at least two parts that are, for example, cylindrical, and that are mounted to move relative to each other to make it possible to put the communication amplification antenna 36 into contact with the distal electrode 18 of the capsule on insertion of the capsule into the first holding element 32, regardless of the length of the distal electrode 18 of the capsule.

For example, to achieve this, a spring element is provided that enables the two parts to move relative to each other.

In another embodiment, the amplification antenna may be formed in one-piece and be constituted by a single, flexible, conductive part.

The springiness of the antenna may be procured by means of a flexible blade or of a blade made of a flexible material, e.g. a flexible conductor wire, or any other compressible means, so as to enable the communication amplification antenna 36 to be put into contact with the distal electrode 18 of the capsule while the capsule is being inserted into the first holding element 32, regardless of the length of the distal electrode 18 of the capsule. For example, the antenna may also be coated with a flexible material such as silicone, it being possible for the coating to give the antenna its springiness.

Preferably, the end of the communication amplification antenna 36 that is in contact with the distal electrode is spherical in order to create contact at a point with the distal electrode and in order to limit the risk of scratching on the covering of the distal electrode, that covering generally being of the titanium nitride (TiN) type.

The communication amplification antenna 36 may be mounted in tight-fitting manner in the holding element. However, in other embodiments, the communication amplification antenna 36 may be snugly fitted, adhesively bonded, crimped, or welded in the first holding element.

As shown in FIGS. 2, 3, 6a, and 6b, the first holding element 32 comprises at least one opening 50 making it possible to see the coupling implemented between the communication amplification antenna 36 and the distal electrode 18 of the capsule. This opening 50 makes it possible, in particular, to check the physical connection between the communication amplification antenna 36 and the distal electrode 18 of the capsule.

In a particular embodiment, the first and the second holding element 32, 34 are designed such that they can be assembled together, in particular by a portion of one holding element being inserted into the other holding element. To this end, the geometrical shapes, in particular of the body of the second holding element and of the body of the first holding element must be complementary, e.g. with functional clearance of 0.1 mm.

FIG. 2 shows the two holding elements as assembled together.

In order to keep the two holding elements securely assembled together, the first and second holding elements 32, 34 comprise complementary locking means suitable for keeping the first holding element locked to the second holding element.

Figure 7A:
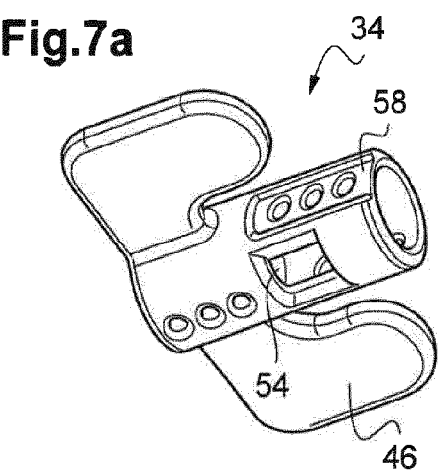
FIGS. 7a and 7b are views of a second holding element in an embodiment of the invention.
Figure 7B:
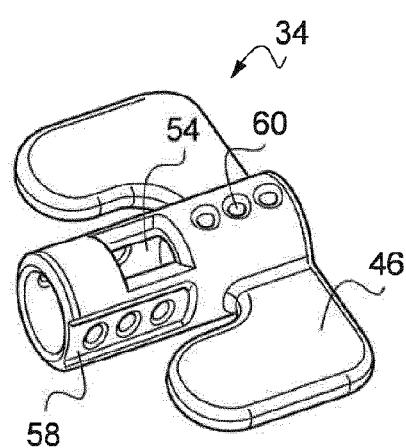

In an embodiment, the locking means 52 of the first holding element are shown in FIGS. 6a and 6b and the locking means 54 of the second holding element are shown in FIGS. 7a and 7b.

The locking means 52 of the first holding element 32 are, for example, constituted by a clip positioned on the inside wall of the cavity 40 in the body of the holding element that receives the distal portion of the capsule, and the complementary locking means 54 of the second holding element 54 are, for example, constituted by an opening, preferably a through opening, of shape complementary to the clip and provided in the wall of the cavity in the body of the second holding element 54 that receives the proximal portion of the capsule.

In a particular embodiment, the first holding element comprise two openings on either side of the locking means, in particular the clip, so as to create a blade 56 that is elastically deformable, that extends from the top of the cavity 40 to the low portion of the cavity, and that is of width slightly larger than the width of the clip.

As shown in FIGS. 7a and 7b, the second holding element comprises at least one groove 58 enabling the clip 52 of the first holding means to slide over a given length, namely the length of the groove, while the two holding elements are being assembled together.

Said at least one groove 58 of the second holding element is, for example, positioned at 90° relative to the locking means 54 of the second holding element.

The groove 58 has a certain length so as to set the depth of assembly of the second holding element 34 inside the first holding element 32.

The first and second holding elements are assembled together using the method described below.

The second holding element is assembled to the first holding element by causing the blade(s) 56 on the first holding element 32 to slide in the grooves 58 in the second holding element, by the clip co-operating with the groove, until it reaches the end of the groove 58. Then, the first holding element is turned relative to the second holding element until the respective locking means of the holding elements are caused to co-operate with each other, e.g. in order to cause the clip 52 on the first holding element to co-operate with the corresponding opening 54 in the second holding element.

The two holding elements are dissembled from each other in the reverse order, i.e. by turning the first holding element relative to the second holding element until the locking clip 52 co-operates with the groove 58 in the second holding element, and then by moving the first holding element in axial translation relative to the second holding element.

In a variant embodiment, the two holding elements are disassembled from each other merely by moving the first holding element in axial translation relative to the second holding element.

In addition, in order to guide the surgeon in manipulating the communication amplification device, the manipulation means are mutually aligned in a horizontal plane when the first and second holding elements are locked together, and the manipulation means 44, 46 form an angle relative to each other when the first and second holding elements are unlocked.

In an embodiment, the opening 54 formed in the second holding means, and able to receive the clip 52 of the first holding means, comprises bevels except on its front face in order to increase the force necessary for disengaging the locking clip 52.

As shown in FIG. 2, at least one of the holding elements, and preferably each of the holding elements, comprises at least one orifice 60 through the capsule-receiving wall of the respective holding element so as to enable fluid to pass through into the communication amplification device, and in particular into the first and second holding means.

This is because, in order to decontaminate the capsule and the holding elements, the assembled assembly is immersed into a decontamination fluid. The orifices 60 present in the walls of the holding elements allow the fluid to pass through over the entire capsule.

In a particular embodiment in which through orifices 60 are formed in the bottom of the groove 58 of the second holding element, corresponding through orifices 60 are then formed in the wall of the first holding element, so that, once the holding elements have been assembled together, the orifices 60 formed at the bottom of the groove correspond substantially to the orifices 60 formed in the wall of the first holding element.

Figure 8:
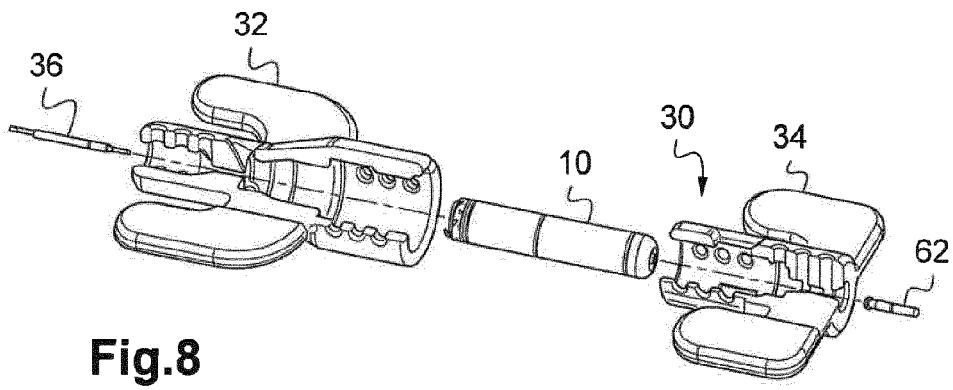
FIG. 8 is a detailed view of the various component elements of a communication amplification device in a second embodiment of the invention.

In a particular embodiment of the invention, the second holding element suitable for receiving the proximal portion of the capsule also comprises a second communication amplification antenna 62 able to be put in contact with the rear element of the capsule that supports the proximal electrode of the capsule, as shown in FIG. 8.

For this purpose, and in a particular embodiment, the second communication amplification antenna 62 is positioned in the second holding element and is kept on the axis along which the capsule 10 is positioned.

Such a communication amplification device 30 making it possible to amplify the signal from the first electrode 18 and from the second electrode 22 of the capsule makes it possible to conduct effective testing on the capsule as inserted in the first and second holding means.

In an embodiment, the second communication amplification antenna 62 is smaller than the first communication amplification antenna 36 that is able to be connected to the distal electrode, in particular since the proximal electrode 22 of the capsule has a larger surface area, of about 40 mm$^2$ and also a larger width, compared with about 2 mm$^2$ for the distal electrode 18.

Figure 9:
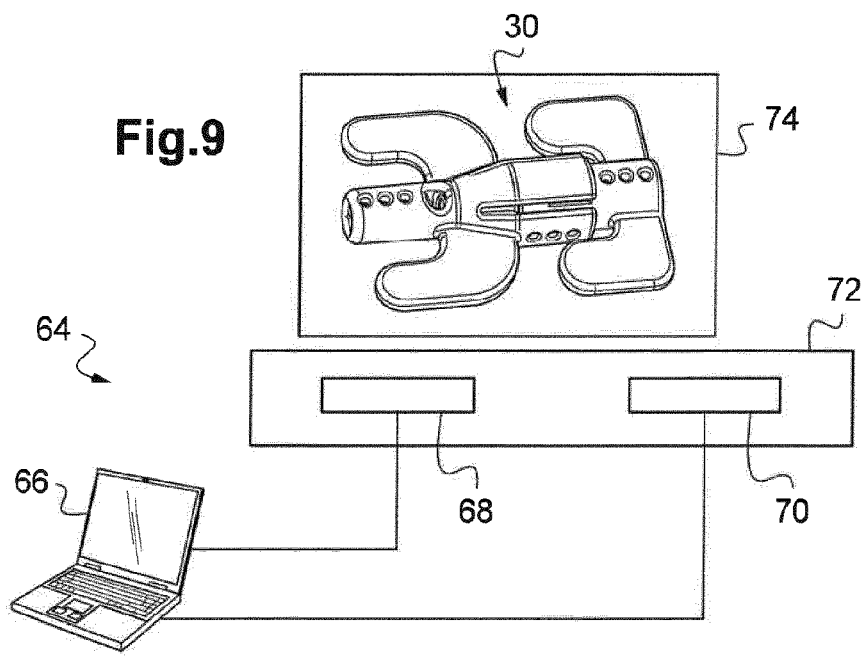
FIG. 9 is a view of apparatus for testing and/or programming a capsule inserted into a communication device of the invention.

FIG. 9 shows testing and/or programming apparatus 64 for testing and programming the capsule as inserted in a communication amplification device 30 of the invention.

This testing and/or programming apparatus 64 comprises an external monitor 66 to which two communication electrodes 68 and 70 are connected. The communication electrodes 68 and 70 are spaced apart by about 20 mm and are inserted in an electrode support 72 in order to achieve effective positioning of the capsule as inserted in the amplification device above the communication electrodes.

In an embodiment of the testing and/or programming apparatus 64, the communication electrodes 68 and 70 are of substantially square area having sides of 25 mm.

If, in a given example, it is considered that the testing and/or programming apparatus 64 comprises a receiver that is sensitive to a level of emitted signal of −100 dB/emitted signal, then coupling of in the range −60 dB to −80 dB is sufficient for good communications between the testing and/or programming apparatus 64 and the capsule 10 as inserted in the communication amplification device 30.

Tests have shown that an antenna length of in the range 10 mm to 20 mm is sufficient to provide the communication distance of 30 mm between the capsule as inserted in the communication amplification device and the communication electrodes.

The FIG. 9 shows such testing and/or programming apparatus 64 on which a communication amplification device incorporating a capsule and as positioned in a sterile bag 74 is positioned at a distance of about 3 mm facing the communication electrodes.

What is claimed is:

1. A communication amplification device for an implantable capsule, in particular for a pacemaker autonomous capsule, the capsule comprising, at its distal end, a distal electrode structured to come into contact with the tissue of a wall of an organ of a patient, said communication amplification device comprising:
a first holding element and a second holding element configured to hold the implantable capsule, wherein the first holding element is configured to receive the distal end of the capsule and the second holding element is configured to receive the proximal end of the capsule, and wherein the first holding element comprises a communication amplification antenna configured to couple to the distal electrode of the capsule, and wherein the communication amplification antenna is an elongated structure that extends away from the distal electrode of the capsule along a central axis of a cavity of the first holding element, wherein:
the first holding element and the second holding element are separable from the implantable capsule, and
the first holding element and the second holding element comprise manipulation elements that extend from one or more sides of each of the first holding element and the second holding element to facilitate separation.

2. The communication amplification device of claim 1, wherein the communication amplification antenna comprises at least two moving parts that are mounted to move relative to each other, and a spring element enabling the two parts to move relative to each other such that the communication amplification antenna is configured to contact the distal electrode of the capsule.

3. The communication amplification device of claim 1, wherein the communication amplification antenna is formed of a flexible conductive part.

4. The communication amplification device of claim 1, wherein the first holding element comprises a receptacle in which the communication amplification antenna is fastened and which comprises a space configured for insertion of and coupling to the distal electrode of the capsule.

5. The communication amplification device of claim 4, wherein the receptacle comprises a shoulder against which turns of an anchor screw of the capsule are configured to come to bear.

6. The communication amplification device of claim 4, wherein the first holding element comprises an opening making it possible to see the coupling configured to be implemented between the communication amplification antenna and the distal electrode of the capsule.

7. The communication amplification device of claim 1, wherein the first holding element and the second holding element are able to be assembled together.

8. The communication amplification device of claim 1, wherein the manipulation elements extend from at least two sides of each of the first holding element and the second holding element.

9. The communication amplification device of claim 1, wherein the first and second holding elements comprise complementary locking elements structured to keep the first holding element and the second holding element locked.

10. The communication amplification device of claim 1, wherein the manipulation elements of the first and second holding elements are aligned in a horizontal plane when the first and second holding elements are locked together, and the manipulation elements of the first and second holding elements form an angle relative to each other when the first and second holding elements are unlocked.

11. The communication amplification device of claim 1, wherein at least one of the first or the second holding element comprises at least one orifice through the wall of said holding element for the purpose of allowing a fluid to pass into the amplification device.

12. The communication amplification device of claim 1, wherein the second holding element comprises a communication amplification antenna configured to contact a proximal electrode of the capsule.

* * * * *